US006978171B2

(12) United States Patent
Goetz et al.

(10) Patent No.: US 6,978,171 B2
(45) Date of Patent: Dec. 20, 2005

(54) AUTOMATED IMPEDANCE MEASUREMENT OF AN IMPLANTABLE MEDICAL DEVICE

(75) Inventors: Steven M. Goetz, Brooklyn Center, MN (US); Jordan A. Barnhorst, Little Canada, MN (US); James M. Hartmann, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 343 days.

(21) Appl. No.: 10/099,436

(22) Filed: Mar. 15, 2002

(65) Prior Publication Data

US 2003/0176807 A1 Sep. 18, 2003

(51) Int. Cl.[7] .............................................. A61B 5/00
(52) U.S. Cl. ..................................................... 600/547
(58) Field of Search ................................ 600/309–310, 600/547; 607/8, 28

(56) References Cited

U.S. PATENT DOCUMENTS

| | | | |
|---|---|---|---|
| 4,425,920 A * | 1/1984 | Bourland et al. ........... 600/485 |
| 5,003,975 A | 4/1991 | Hafelfinger | |
| 5,058,583 A * | 10/1991 | Geddes et al. .............. 600/547 |
| 5,246,008 A * | 9/1993 | Mueller ...................... 600/508 |
| 5,507,786 A | 4/1996 | Morgan | |
| 5,534,018 A | 7/1996 | Wahlstrand | |
| 5,607,455 A * | 3/1997 | Armstrong ...................... 607/8 |
| 5,626,620 A | 5/1997 | Kieval et al. | |
| 5,720,293 A * | 2/1998 | Quinn et al. ................. 600/505 |
| 5,741,311 A | 4/1998 | McVenes | |
| 5,755,742 A | 5/1998 | Schuelke | |
| 5,855,594 A | 1/1999 | Olive et al. | |
| 5,891,179 A | 4/1999 | Er | |
| 6,044,301 A | 3/2000 | Hartlaub et al. | |
| 6,208,894 B1 | 3/2001 | Schulman et al. | |
| 6,317,628 B1 * | 11/2001 | Linder et al. ............... 600/547 |
| 6,360,123 B1 * | 3/2002 | Kimchi et al. .............. 600/547 |
| 6,490,481 B1 * | 12/2002 | Komatsu et al. ............ 600/547 |
| 6,725,087 B1 * | 4/2004 | Rubinsky et al. ........... 600/547 |
| 6,760,624 B2 * | 7/2004 | Anderson et al. ............. 607/28 |
| 2001/0037132 A1 | 11/2001 | Whitehurst et al. | |
| 2002/0002389 A1 * | 1/2002 | Bradley et al. ................. 607/8 |

FOREIGN PATENT DOCUMENTS

WO    WO 99/65568    12/1999

* cited by examiner

*Primary Examiner*—Eric F. Winakur
*Assistant Examiner*—Matthew Kremer
(74) *Attorney, Agent, or Firm*—Banner & Witcoff, Ltd.

(57) ABSTRACT

The present invention automates impedance measurements between pairs of electrodes that are associated with a lead of an implanted device. Apparatus comprises a communications module and a processor, in which the processor communicates with the implanted device over a communications channel. The processor instructs the implanted device to perform a voltage measurement that is associated with a stimulation pulse between the pair of electrodes. The implanted device sends the voltage measurement to the apparatus over the communications channel from which the apparatus determines the impedance between the pair of electrodes. The apparatus initiates an impedance measurement for each pair of electrodes along the lead. With a plurality of leads, the apparatus repeats the impedance measurements for electrode pairs of the other leads. The embodiment also supports measuring a current between pairs of electrodes. The impedance measurements and current measurements are displayed to a clinician on a user interface.

20 Claims, 10 Drawing Sheets

AUTOMATED IMPEDANCE MEASUREMENT OF AN IMPLANTABLE MEDICAL DEVICE

RELATED APPLICATION

This disclosure is related to the following co-pending application entitled "AMPLITUDE RAMPING OF WAVEFORMS GENERATED BY AN IMPLANTABLE MEDICAL DEVICE" by inventor Goetz, et al., having U.S. patent application Ser. No. 10/099,438, and filed on Mar. 15, 2002, which is not admitted as prior art with respect to the present disclosure by its mention in this section.

FIELD OF THE INVENTION

This invention relates generally to implantable medical devices, and more particularly to the measurement of the impedance of implantable medical devices.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

One type of implantable medical device is an Implantable Neuro Stimulator (INS). The INS delivers mild electrical impulses to neural tissue using an electrical lead. The neurostimulation targets desired neural tissue to treat the ailment of concern. For example, in the case of pain, electrical impulses (which are felt as tingling) may be directed to cover the specific sites where the patient is feeling pain. Neurostimulation can give patients effective pain relief and can reduce or eliminate the need for repeat surgeries and the need for pain medications.

Implantable medical devices such as neurostimulation systems may be partially implantable where a battery source is worn outside the patient's body. This system requires a coil and/or an antenna to be placed on the patient's skin over the site of the receiver to provide energy and/or control to the implanted device. Typically, the medical device is totally implantable where the battery is part of the implanted device. The physician and patient may control the implanted system using an external programmer. Such totally implantable systems include, for example, the Itrel® 3 brand neurostimulator sold by Medtronic, Inc. of Minneapolis, Minn.

In the case of an INS, for example, the system generally includes an implantable neurostimulator (INS) (also known as an implantable pulse generator (IPG)), external programmer(s), and electrical lead(s). The INS is typically implanted near the abdomen of the patient. The lead is a small medical wire with special insulation. It is implanted next to the spinal cord through a needle and contains a set of electrodes (small electrical contacts) through which electrical stimulation is delivered to the spinal cord. The lead is coupled to the INS via an implanted extension cable. The INS can be powered by an internal source such as a battery or by an external source such as a radio frequency transmitter. The INS contains electronics to send precise, electrical pulses to the spinal cord, brain, or neural tissue to provide the desired treatment therapy. The external programmer is a hand-held device that allows the physician or patient to optimize the stimulation therapy delivered by the INS. The external programmer communicates with the INS using radio waves.

One of the key troubleshooting tools for the clinicians for the stimulation devices is the lead impedance measurement. This measure is basically the electrical resistance of the leads plus that of the tissue contacts and provides important information regarding both the lead placement and the integrity of the lead itself.

A lead contains a plurality of electrodes, e.g. four electrodes. Some of the electrodes may be configured as being inactive. In previous programmer implementations, lead measurements were provided only for the currently programmed electrode configurations. Though this in itself provides some utility, various lead problems may be undetected. For example, an active electrode that is shorting to one or more inactive electrodes will not be detected by a single measurement such as previously provided.

Some clinicians circumvent this limitation by manually configuring each electrode pair and performing the single measure many times. For example, with a lead containing four electrodes, there are six electrode pairs (4!/(2!2!)). The number substantially increases as the number of electrodes increases. With a lead containing eight electrodes, there are twenty-eight electrode pairs (8!/(6!2!)). Each pair of electrodes requires that the clinician execute a number of operations through an input device. While efficacious, this manual process proves to be time consuming and tedious. Furthermore, all such measurements are performed at the current therapy settings, which may not be optimal for measurement accuracy and for the patient's comfort.

BRIEF SUMMARY OF THE INVENTION

In the first embodiment of the invention, method and apparatus automates impedance measurements of sets of electrodes that are associated with a lead of an implanted device. The implanted device may support a plurality of leads. Apparatus comprises a communications module and a processor, in which the processor communicates with the implanted device over a communications channel through the communications module. The processor instructs the implanted device to perform a voltage measurement that is associated with a stimulation pulse of the set of electrodes. The implanted device sends the voltage measurement to the apparatus over the communications channel from which the apparatus determines the impedance of the set of electrodes. The apparatus initiates an impedance measurement for each set of electrodes along the lead that is associated with the implanted device. With a plurality of leads, the apparatus repeats the impedance measurements for electrode sets of the other leads. The embodiment also supports measuring a current of a set of electrodes. The impedance measurements and current measurements are displayed to a clinician on a user interface.

Alternative embodiments of the invention may support a user interface that is external to the apparatus. Also, alternative embodiments may store the measurements rather than display the measurements on the user interface.

DETAILED DESCRIPTION OF THE INVENTION

Figure 1:
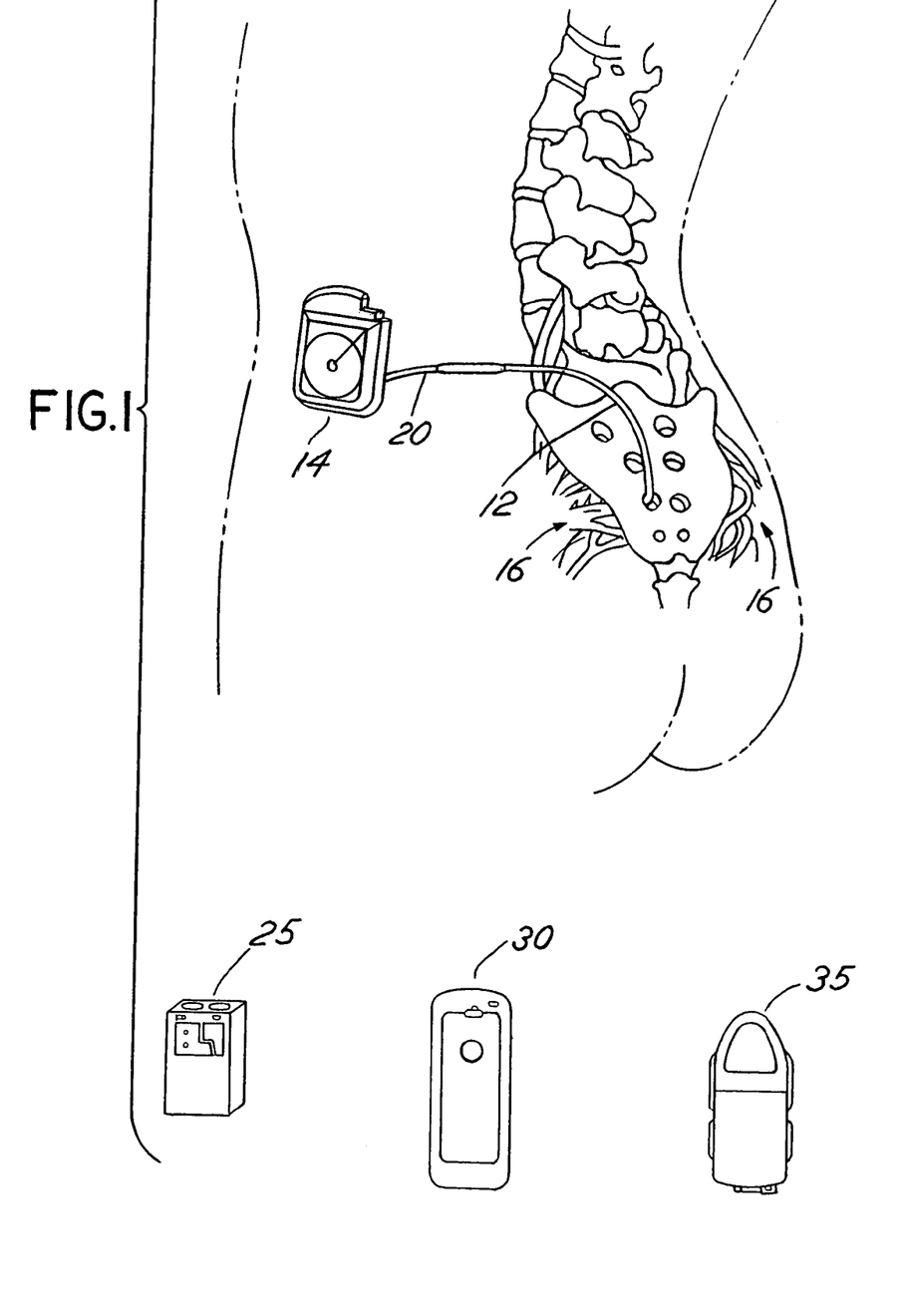
FIG. 1 illustrates an implantable medical device in accordance with an embodiment of the present invention, as implanted in a human body.

FIG. 1 shows the general environment of an Implantable Neuro Stimulator (INS) medical device 14 in accordance with a preferred embodiment of the present invention. The neurostimulation system generally includes an INS 14, a lead 12, a lead extension 20, an External Neuro Stimulator (ENS) 25, a physician programmer 30, and a patient programmer 35. The INS 14 preferably is a modified implantable pulse generator that will be available from Medtronic, Inc. with provisions for multiple pulses occurring either simultaneously or with one pulse shifted in time with respect to the other, and having independently varying amplitudes and pulse widths. The INS 14 contains a power source and electronics to send precise, electrical pulses to the spinal cord, brain, or neural tissue to provide the desired treatment therapy. In the embodiment, INS 14 provides electrical stimulation by way of pulses although alternative embodiments may use other forms of stimulation such as continuous electrical stimulation.

The lead 12 is a small medical wire with special insulation. The lead 12 includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 12 may also be a paddle having a plurality of electrodes including, for example, a Medtronic paddle having model number 3587A. In yet another embodiment, the lead 12 may provide electrical stimulation as well as drug infusion. Those skilled in the art will appreciate that any variety of leads may be used to practice the present invention.

The lead 12 is implanted and positioned to stimulate a specific site in the spinal cord or the brain. Alternatively, the lead 12 may be positioned along a peripheral nerve or adjacent neural tissue ganglia like the sympathetic chain or it may be positioned to stimulate muscle tissue. The lead 12 contains one or more electrodes (small electrical contacts) through which electrical stimulation is delivered from the INS 14 to the targeted neural tissue. If the spinal cord is to be stimulated, the lead 12 may have electrodes that are epidural, intrathecal or placed into the spinal cord itself. Effective spinal cord stimulation may be achieved by any of these lead placements.

Although the lead connector can be connected directly to the INS 14, typically the lead connector is connected to a lead extension 20 which can be either temporary for use with an ENS 25 or permanent for use with an INS 14. An example of the lead extension 20 is Model 7495 available from Medtronic.

The ENS 25 functions similarly to the INS 14 but is not designed for implantation. The ENS 25 is used to test the efficacy of stimulation therapy for the patient before the INS 14 is surgically implanted. An example of an ENS 25 is a Model 3625 Screener available from Medtronic.

The physician programmer 30, also known as a console programmer, uses telemetry to communicate with the implanted INS 14, so a physician can program and manage a patient's therapy stored in the INS 14 and troubleshoot the patient's INS system. An example of a physician programmer 30 is a Model 7432 Console Programmer available from Medtronic. The patient programmer 35 also uses telemetry to communicate with the INS 14, so the patient can manage some aspects of her therapy as defined by the physician. An example of a patient programmer 35 is a Model 7434 Itrel® 3 EZ Patient Programmer available from Medtronic.

Those skilled in the art will appreciate that any number of external programmers, leads, lead extensions, and INSs may be used to practice the present invention.

Implantation of an Implantable Neuro Stimulator (INS) typically begins with implantation of at least one stimulation lead 12 usually while the patient is under a local anesthetic. The lead 12 can either be percutaneously or surgically implanted. Once the lead 12 has been implanted and positioned, the lead's distal end is typically anchored into position to minimize movement of the lead 12 after implantation. The lead's proximal end can be configured to connect to a lead extension 20. If a trial screening period is desired, the temporary lead extension 20 can be connected to a percutaneous extension with a proximal end that is external to the body and configured to connect to an External Neuro Stimulator (ENS) 25. During the screening period the ENS 25 is programmed with a therapy and the therapy is often modified to optimize the therapy for the patient. Once screening has been completed and efficacy has been established or if screening is not desired, the lead's proximal end or the lead extension proximal end is connected to the INS 14. The INS 14 is programmed with a therapy and then implanted in the body typically in a subcutaneous pocket at a site selected after considering physician and patient preferences. The INS 14 is implanted subcutaneously in a human body and is typically implanted near the abdomen of the patient.

Figure 2A:
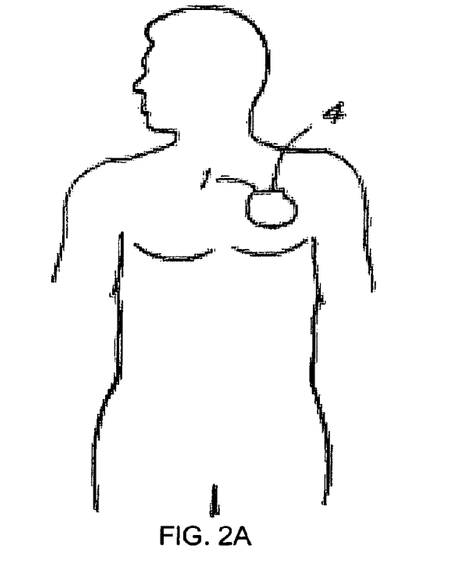
FIGS. 2A–D illustrates locations where the implantable medical device of the present invention can be implanted in the human body other than the location shown in FIG. 1.
Figure 2B:
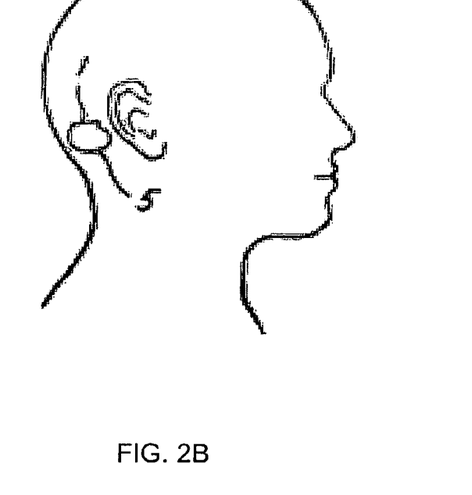
Figure 2C:
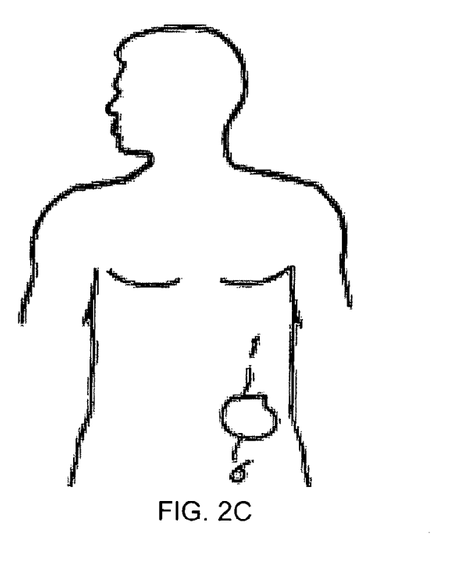
Figure 2D:
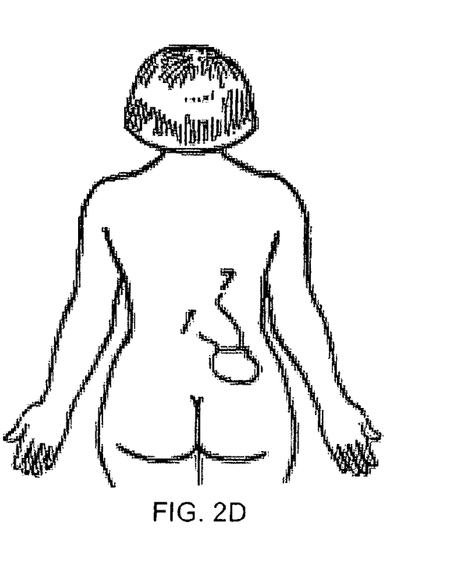

The above embodiment for the placement of the INS 14 within the lower left abdominal region 6 of the patient is further illustrated in FIG. 2C. Other preferred embodiments for the placement of stimulator 1 within a human patient is further shown in FIGS. 2A, 2B, and 2D. As shown in FIG. 2A, the INS 14 can be implanted in a pectoral region 4 of the patient. As shown in FIG. 2B, the INS 14 can be implanted in a region 5 behind the ear of a patient, and more specifically in the mastoid region. As shown in FIG. 2D, the INS 14 can be placed in the lower back or upper buttock region 7 of the patient. The INS 14 is discussed in further detail herein.

The physician periodically uses the physician programmer 30 to communicate with the implanted INS 14 to manage the patient therapy and collect INS data. The patient uses the patient programmer 35 to communicate with the implanted INS 14 to make therapy adjustment that have been programmed by the physician, recharge the INS power source, and record diary entries about the effectiveness of the therapy. Both the physician programmer 30 and patient programmer 35 have an antenna or coil locator that indicates when the telemetry head is aligned closely enough with the implanted INS 14 for adequate telemetry.

Optionally, the neurostimulation system may include a sensor 25 to provide closed-loop feedback control of the INS 14. For example, the INS 14 may receive feedback instructions from an external component, which processes a recorded signal from the sensor 25 and sends instruction to signal generator via antenna.

Figure 3:
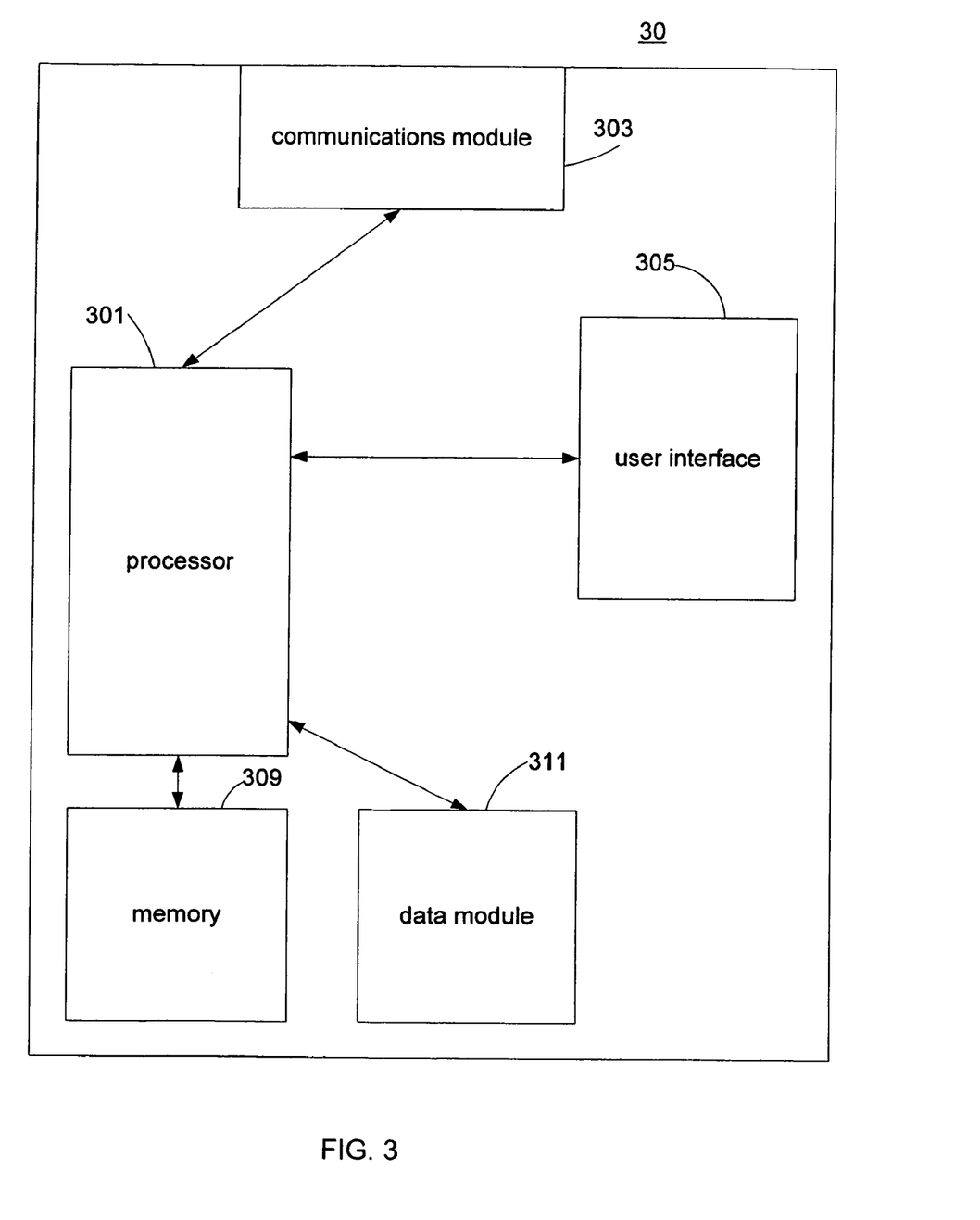
FIG. 3 shows an architecture of a programmer in accordance with an embodiment of the present invention.

FIG. 3 shows an architecture of the programmer 30 in accordance with an embodiment of the present invention. A processor 301 communicates to the INS 14 through a communications module 303 over a radio channel. With alternative embodiments, the communications module 303 can correspond to other types of communications channels, including an infrared (IR) channel and a cabled channel. In the embodiment, the communications module 303 provides communications from the processor 301 to the INS 14 and from the INS 14 to the processor 301 (i.e. two-way communications.) Thus, the processor 301 can command the INS 14 to perform an action, and the INS 14 can consequently return a response to the processor 301. The processor 301 displays information to a user and receives responses and commands from the user, e.g. a clinician, through a user interface 305. The programmer 30 comprises the user interface 305 in the embodiment. The clinician inputs information and commands through a touch-sensitive screen, although an alternative embodiment can utilize other input devices such as a keyboard or can utilize a voice recognition capability to identify inputs articulated by the clinician. Also, an alternative embodiment can implement the user interface 305 that is external to processor, e.g. with a laptop computer through a data port. In another alternative embodiment, the processor 301 stores the impedance measurements in a memory 309 for later retrieval by the clinician. The processor 301 executes computer instructions that are contained in the memory 309. Patient data, e.g. parameter settings of the INS 14 is contained in a data module 311, which is a pluggable memory device. However, an alternative embodiment can store patient data in the memory 309 utilizing a data structure.

Figure 4:
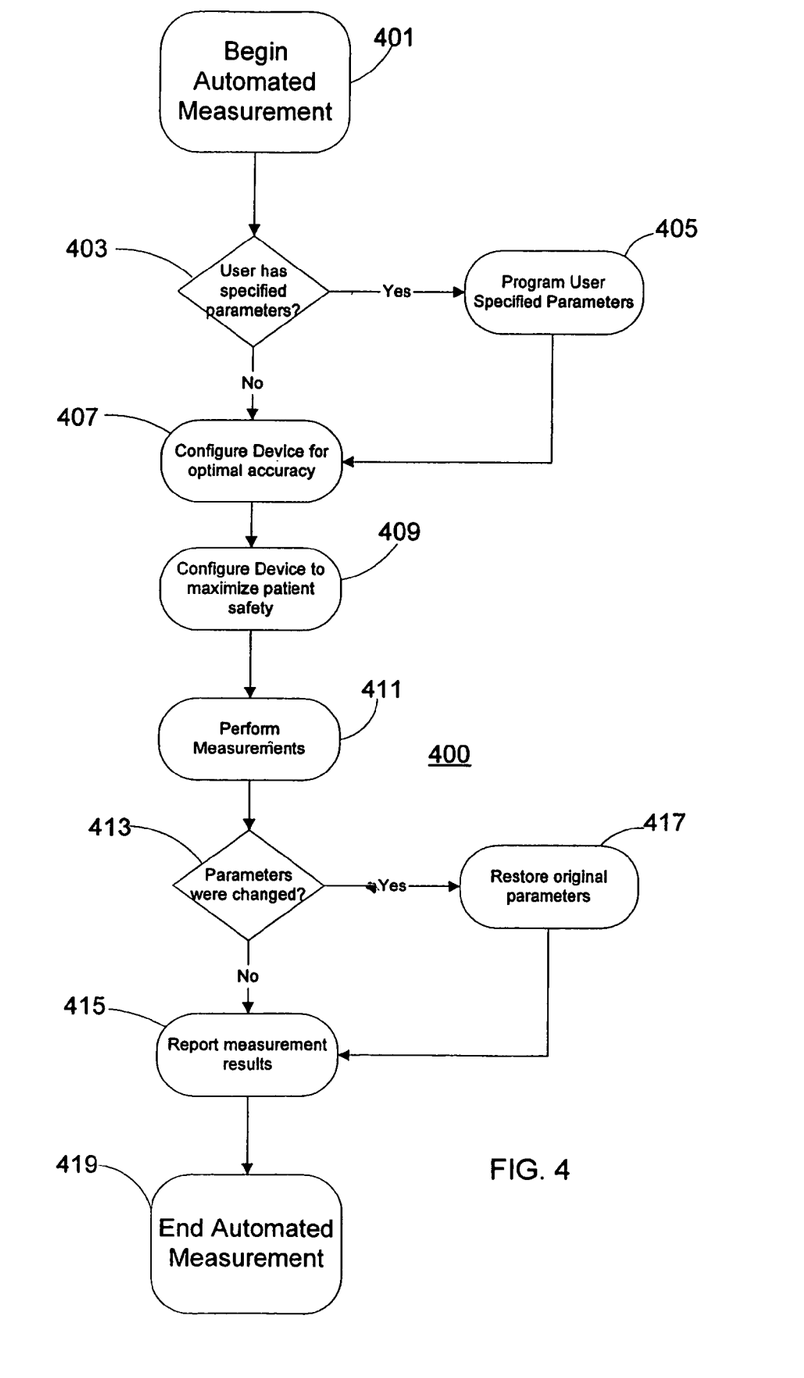
FIG. 4 shows a flow diagram for an automated process for measuring an impedance between electrodes of an implantable lead.

FIG. 4 shows a flow diagram for an automated process for measuring an impedance between a pair of electrodes contained on the implantable lead 12, thus providing an automated impedance measurement capability. Variations of the embodiment support a measurement of an impedance of a set of electrodes, in which the set comprises more than two electrodes. With one variation of the invention, a trio of electrodes comprising an anode and two surrounding cathodes are configured to provide a therapy configuration. In the flow diagram shown in FIG. 4, the impedance between each pair of electrodes is measured, in which the other electrodes are turned-off (deactivated). Measurements are repeated for other pairs of electrodes. Knowing the impedance between each pair of electrodes verifies the integrity of all electrodes and the placement of the lead 12, which contains the electrodes. The device 14 can be associated with more than one lead. In such a case, an impedance measurement process 400 measures the impedance between each pair of configured electrodes for each lead. The corresponding computer-executable instructions are executed by the processor 301 by accessing the memory 309. The automated impedance measurement capability allows the specification of a special parameter set used only for measurements. If no special settings are selected, a default set that is selected by the programmer 30 for optimal performance is used instead.

Once the impedance measurement process 400 is started, the implanted device is configured by the programmer 30 with these parameters and other parameters of the device 14 are adjusted to enhance measurement accuracy and patient safety. The measurement process 400 then proceeds, algorithmically selecting electrode pairs for measurement based on the type of device (associated with device 14) that is detected and information about device's lead 12 configuration previously entered by the implanting physician and stored by programmer 30 in a Patient Profile record contained in the data module 311. As the measurement process 400 progresses, the resulting information is presented on screen to the user along with an indication of the progress. At the end of the measurement process 400, all parameters are reset to their pre-measurement settings (if, indeed, they were changed). Following the measurement completion, the data is displayed onscreen (corresponding to the user interface 305) and is placed in the printed and saved reports. This data remains valid until the end of the session or until the clinician changes the configuration of the device (i.e. by selecting one active lead instead of two, etc.).

In step 403, the processor 301 determines if the user (clinician) has specified parameters for the impedance measurement. In some cases the clinician may have experience with a particular set of parameters. If so, the processor 301 inputs the parameters through the user interface 305 in step 405. For example, the clinician can set some of the parameters such as pulse width. (The screen shown in FIG. 7 enables the clinician to set the pulse width, pulse amplitude, and the pulse rate of the stimulating pulses during the measurement process 400.) If not, the processor 301 will utilize predetermined parameters in accordance the device type of the implanted device 14 in step 407. (The INS 14 provides an identification of the device type through the communications channel when interrogated by the programmer 30.)

In step 409, the processor 301 configures parameters (other than the specified parameters associated with step 405) to match the characteristics of the device type. Because the automated process shown in FIG. 4 can measure an impedance between each pair of electrodes that is configured on the lead 12, electrodes, other than the electrode pair currently being measured, are turned off. During the transition of configuring active electrodes during the measurement process 400, parameters may be adjusted (e.g. zeroing the pulse amplitude) in step 409. Also, in step 409, some of the features of the device 14 (e.g. cycling of stimulation pulses that may be utilized for conserving the battery of the implanted device 14) may be deactivated during the process 400 in order to enhance the patient's comfort.

Figure 5:
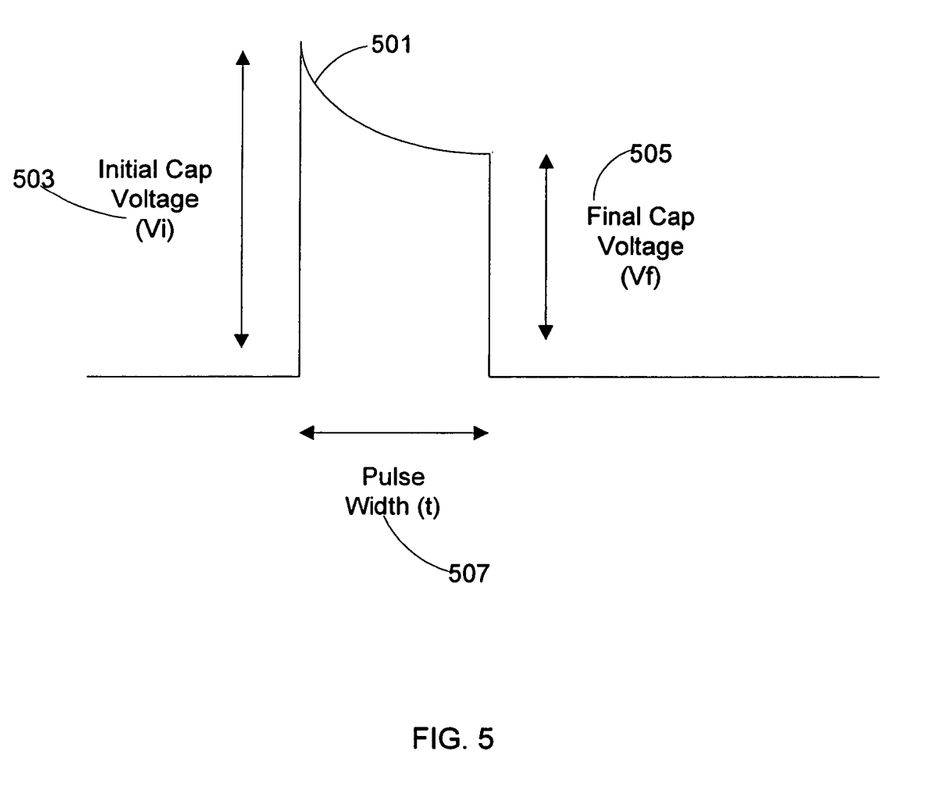
FIG. 5 shows a pulse waveform utilized for measuring an impedance between a pair of electrodes on a lead.
Figure 6:
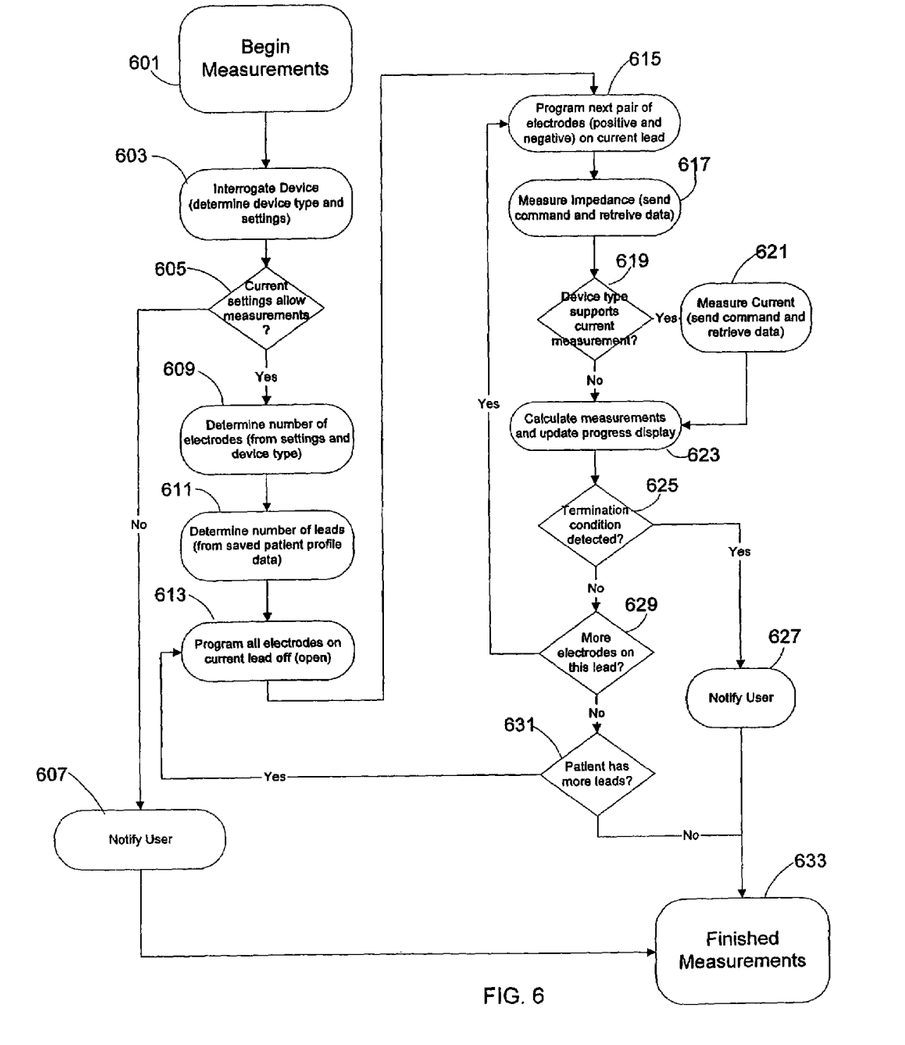
FIG. 6 shows a flow diagram for performing impedance measurements between electrodes of an implantable lead.

In step 411, the processor 301 performs an impedance measurement for each measurement iteration of the process 400 (corresponding to each electrode pair). In FIG. 6 is a detailed flow diagram corresponding to step 411 and will be discussed later. In the embodiment, the processor 301 instructs the device 14 to measure a final voltage ($V_f$) 505 of a stimulation waveform 501 by sending a command over the communications channel through the communications module 303. The processor 301 has knowledge of a pulse width 507 of the waveform 501 (corresponding to a setting 711 in FIG. 7) and an initial voltage ($V_i$) 503 (corresponding to a setting 709) that the processor 301 previously sent to the device 14 in steps 405 and 407 over the communications channel.

The impedance measurement between two electrodes is based on an electrical model that is characterized by an equivalent capacitor and an equivalent resistor so that $$V_f = V_i * e^{-T/RC} \qquad (EQ. 1),$$

where R is the value of the equivalent resistor and C is the value of the equivalent capacitor, and T is the pulse width 507. The processor 301 determines R (which is the impedance of the assumed electrical model of the embodiment) by:

$$R = T/(C * \ln(V_i/V_f)) \qquad (EQ. 2),$$

where C is known as a function of the device type (device 14).

Alternative embodiments may model the electrical characteristics between a pair of electrodes differently and may use implanted devices that have different electrical characteristics. Consequently, alternative embodiments may determine the impedance utilizing a corresponding mathematical formula.

When the impedance measurements have been completed in step 411, step 413 determines if any parameters that are associated with the device 14 were modified during the measurement process 400. If so, the parameters are restored in step 417. The impedance measurements are displayed on the user interface 305 in step 415.

FIG. 6 shows a flow diagram for performing impedance measurements between electrodes of the implantable device 14. Measurement process 600 is initiated with step 601. In step 603, the processor 301 interrogates the device 14 over the communications channel in order to determine the service type and the settings. Step 603 verifies the results in step 405 because the placement of the device 14 and the lead 12 may change as a result of body movement during the execution of the process 400. If step 605 determines that the current settings (as configured by steps 405 and 407) are not correct to allow an impedance measurement, the clinician is notified in step 607 so that the settings can be reconfigured by repeating steps 403 to 409.

If step 605 determines that the settings are correct, the number of electrodes are determined from the settings and the device type in step 609. In step 611 the number of leads is obtained from patient profile data that is stored in the data module 311. (For example, the device 14 may be able to support two leads even though the physician has implanted only one lead.)

In step 613, all electrodes of the lead 12 are de-activated in preparation of the impedance measurement. (The processor 301 sends a corresponding command over the communications channel to the device 14.) In step 615, the processor 301 activates the next pair of electrodes. In step 617, the processor 301 sends a command to the device 14 to measure and return the voltage $V_f$ 505. Because the processor 301 knows T, C, and $V_i$, the processor 301 calculates the impedance between the pair of electrodes using Equation 2.

In step 619, the processor 301 determines whether the device 14 can support measuring the current between the pair of electrodes from the device type (as obtained in step 603). (Variations of the embodiment support a measurement of an impedance of a set of electrodes, in which the set comprises more than two electrodes.) If so, the processor 301 commands the device 14 to return the corresponding measurement over the communications channel in step 621. The measurement of the current is used as a crosscheck to the impedance measurement in order to verify the integrity of the electrode pair. (This crosscheck is useful when a patient has a plurality of implanted devices in which leakage current can occur between the devices.) The values of the impedance and the current are consequently displayed on the user interface 305 in step 623.

In step 625, the processor 301 determines if the impedance measurements have been completed, cancelled, or terminated for the pairs of electrodes. If so, the clinician is notified in step 627 through the user interface 305. Otherwise, the processor 301 determines if another electrode pair should be measured in step 629. If so, step 615 is repeated. If not, processor determines if another lead (that is associated with the device 14) needs to be evaluated in step 631. If so, step 613 is repeated. If not, the process 600 is completed in step 633.

FIGS. 7, 8, 9, 10 show exemplary screens that are displayed at the user interface 305 for supporting automated impedance measurements in accordance with an embodiment of the present invention.

Figure 7:
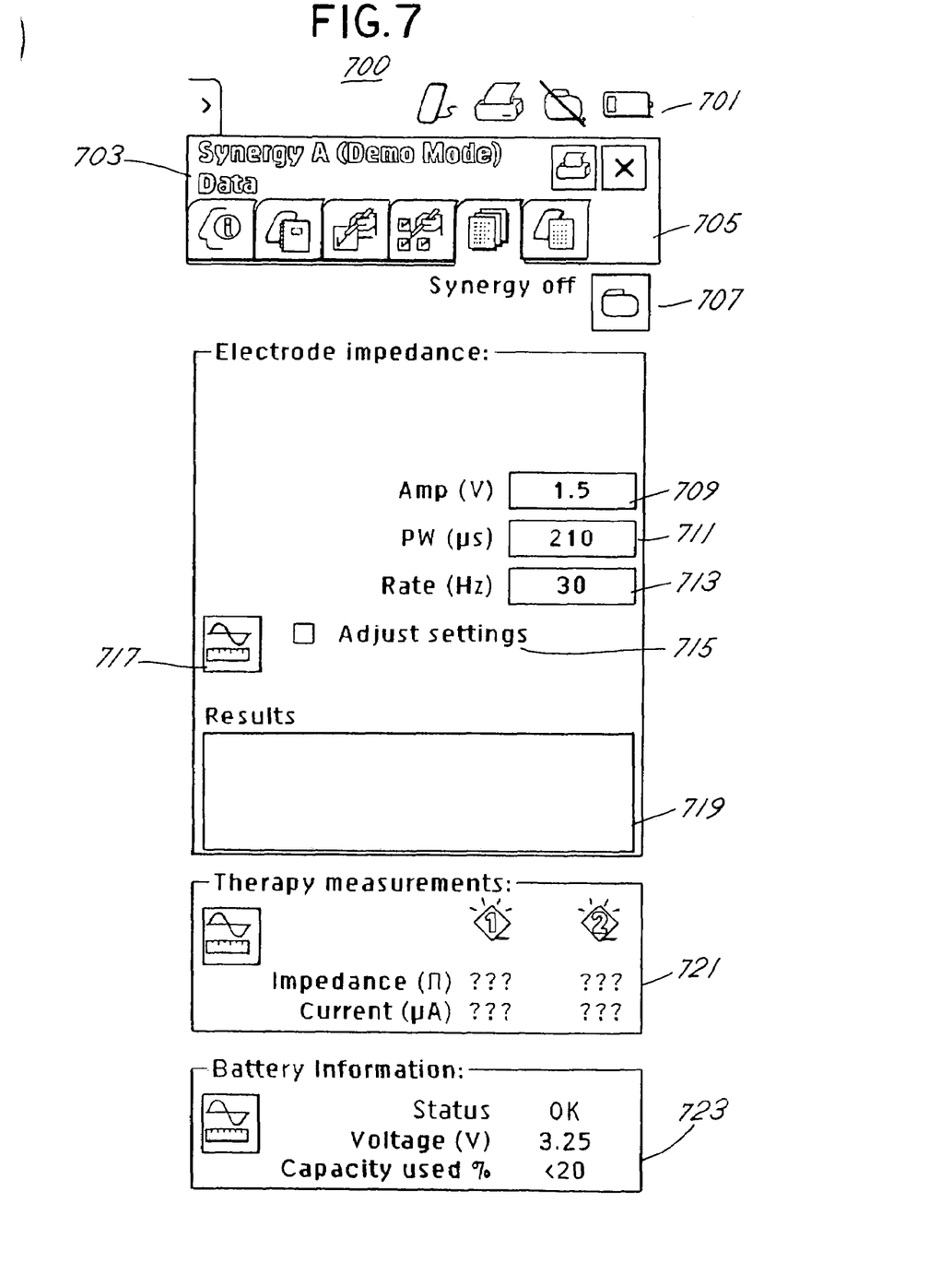
FIG. 7 shows a data tab screen that is displayed on a user interface.
Figure 8:
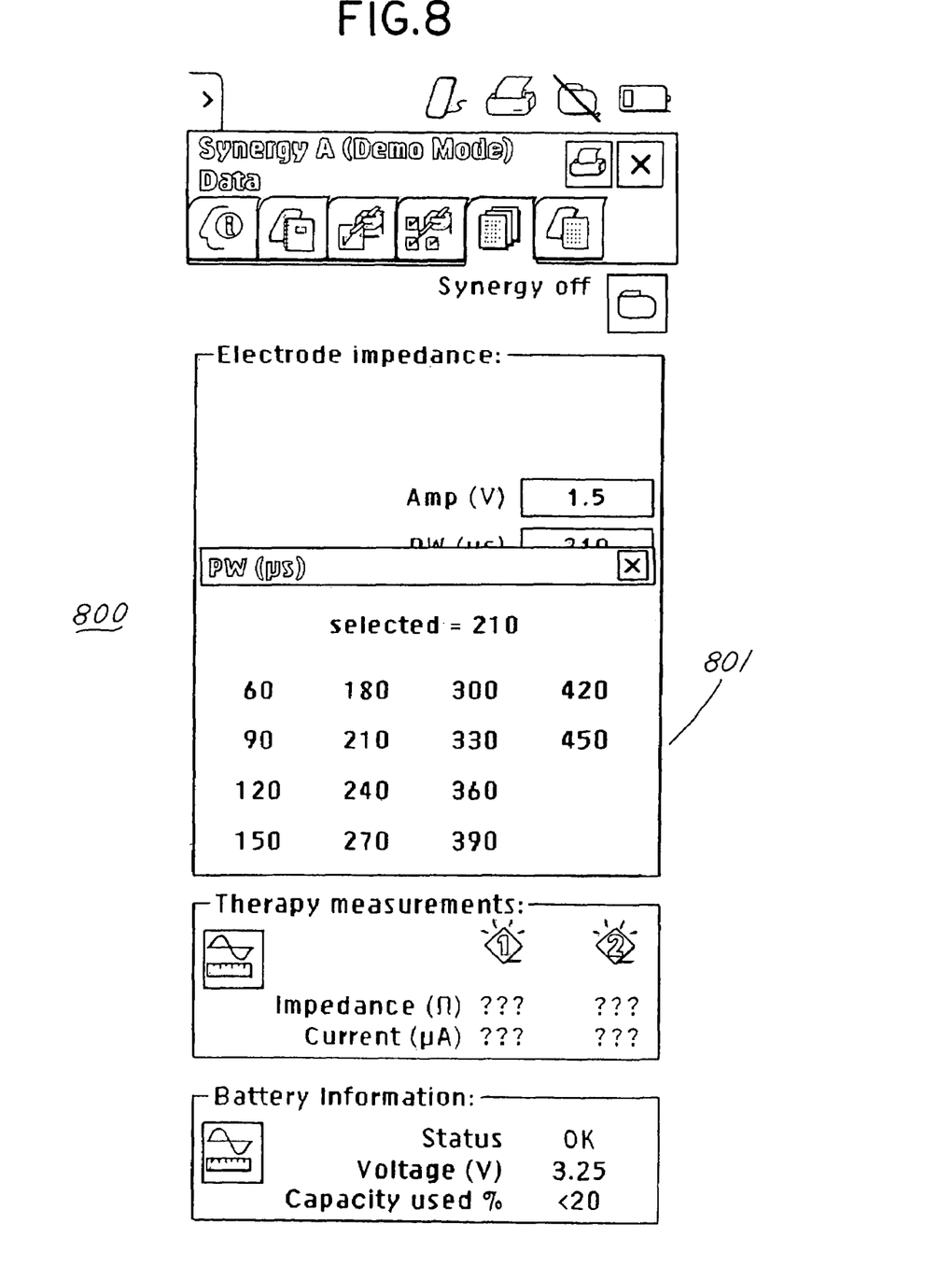
FIG. 8 shows an adjustment of settings screen that is displayed on a user interface.

FIG. 7 shows a data tab screen 700 that is displayed on a user interface 305. A status bar 701 indicates the status of the programmer 30. Examples of the status include a communications module status, a printer status, and a battery status. A title bar 703 comprises a device type (corresponding to the device 14), mode of operation (e.g. demo mode), and a screen name. A screen tabs field 705 allows the clinician to select a patient profile screen, quick look, screen, programming screen, special screen, or data screen. A field 707 activates or deactivates the implanted device 14. In FIG. 7, the data screen is selected. Fields 709, 711, and 713 correspond to the amplitude, pulse width, and pulse rate of the stimulation pulses that are utilized during the process 400, respectively. However, the clinician can adjust the settings through a field 715. (An example of adjusting the pulse with is shown in FIG. 8. The clinician can choose a pulse width by selecting a value in a field 801.) Once the settings have been established for the process 400, the clinician can initiate the process 400 through a field 717. When the process 400 is executing or has completed execution, the results are displayed in an area 719. An area 721 provides impedance and stimulation current measurements at currently programmed (actual) device parameters (if the clinician has selected these measurements). A battery information area 723 provides neurostimulator battery status information.

Figure 9:
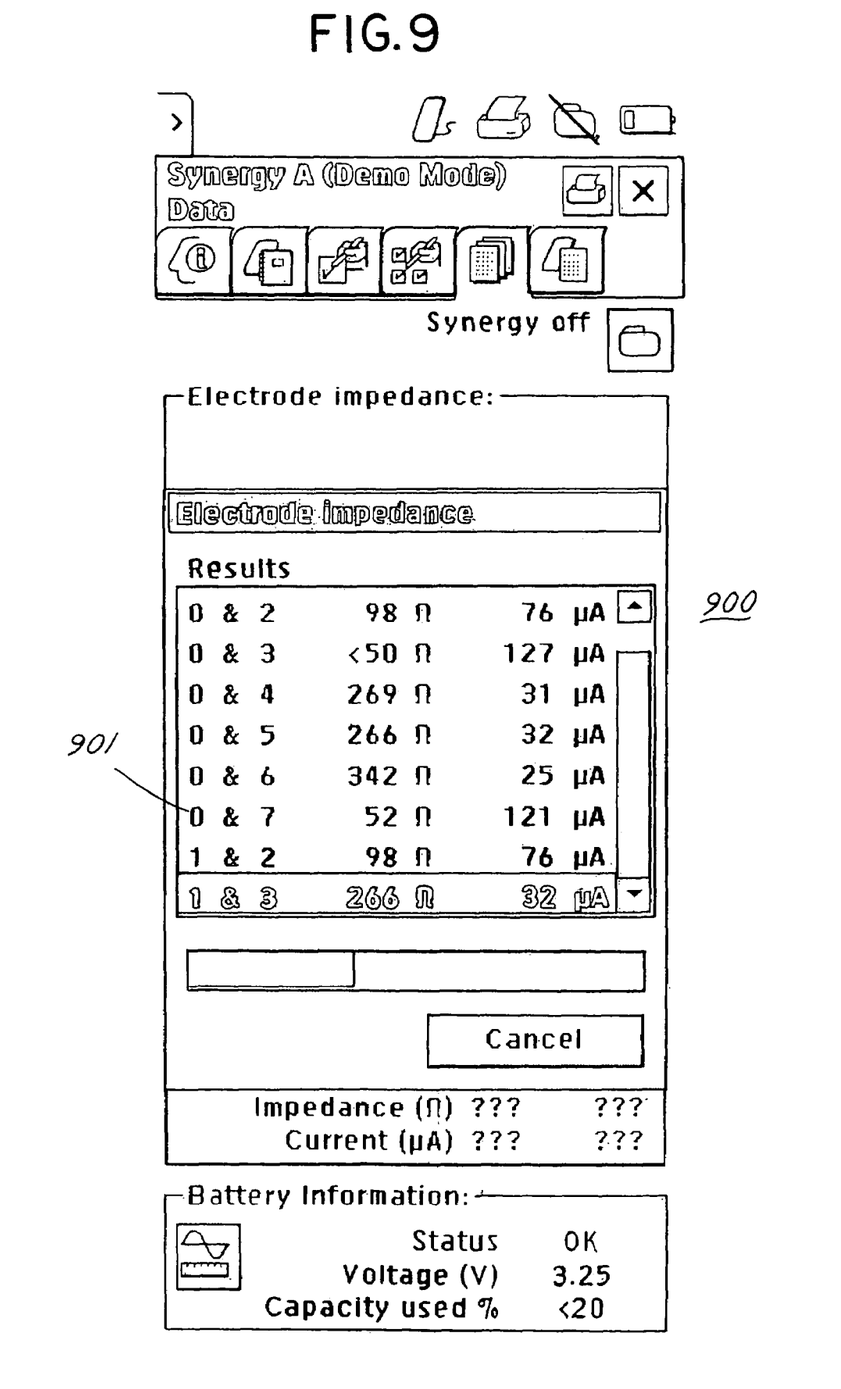
FIG. 9 shows a measurements in progress screen that is displayed on a user interface.

FIG. 9 shows measurements in a progress screen 900 that is displayed on the user interface 305. As the process 400 is executing, impedance measurements are displayed in an area 901 (corresponding to the area 719 in FIG. 7). Each entry provides an identification of electrodes for an electrode pair, an associated value of impedance, and a value of current that is measured between the electrodes of the pair.

Figure 10:
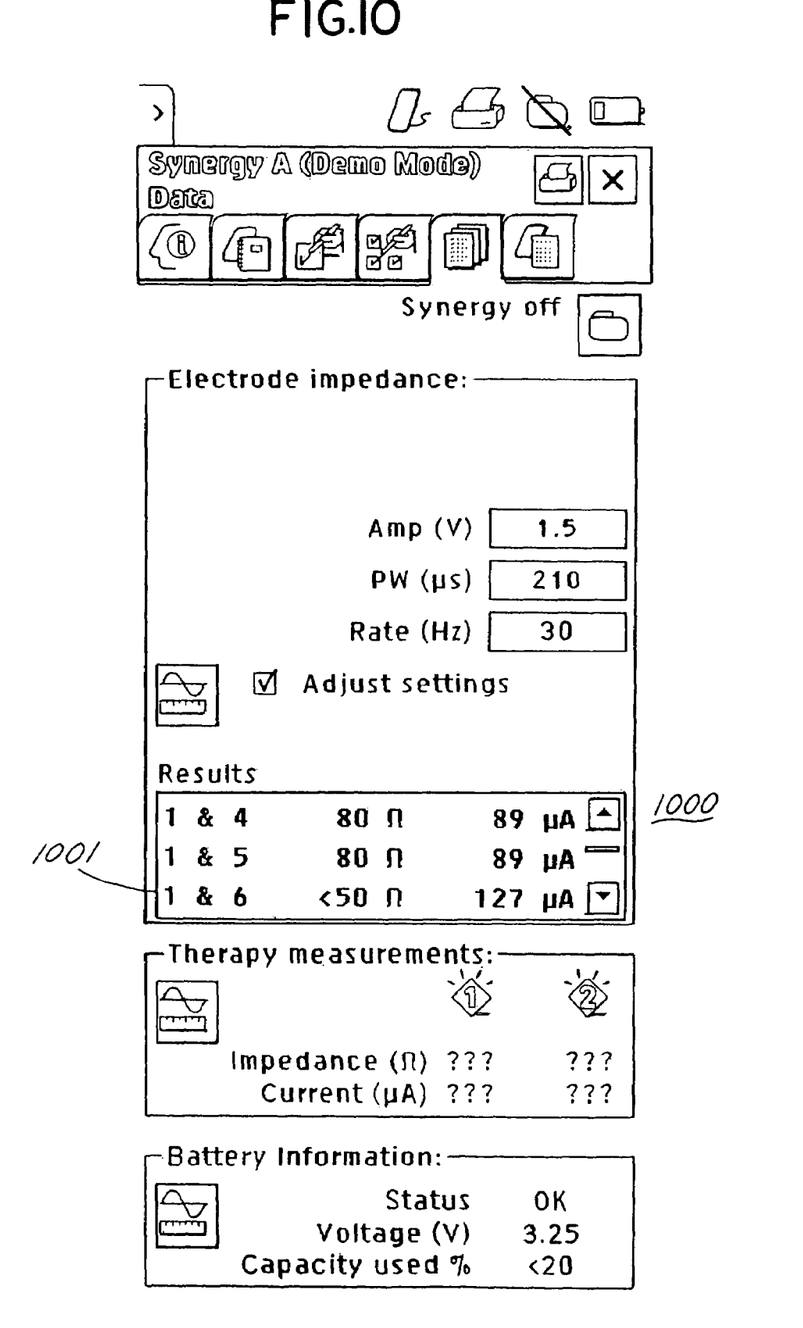
FIG. 10 shows a measurements results screen that is displayed on a user interface.

FIG. 10 shows a measurements results screen 1000 that is displayed on the user interface 305. An area 1001 provides the results of the process 400 upon completion of the process 400.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Thus, embodiments of the AUTOMATED IMPEDANCE MEASUREMENT OF AN IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for automating impedance measurements associated with an implanted device, the method comprising:
   (a) configuring a parameter of a stimulation pulse of the implanted device;
   (b) performing a measurement process with the stimulation pulse in order to determine an impedance value corresponding to at least one electrode comprising:
      (i) instructing the implanted device to perform a measurement that is associated with the at least one electrode, wherein the at least one electrode is contained on a lead;
      (ii) calculating the impedance value utilizing the measurement, wherein (i) and (ii) are repeated for each at least one other electrode that is associated with the lead; and
      (iii) upon completion of (i) and (ii), restoring an original value of the parameter; and
   (c) automatically processing the impedance value.

2. The method of claim 1, wherein the at least one electrode comprises at least eight electrodes.

3. The method of claim 1, wherein (c) comprises:
   (i) displaying the impedance value on a user interface.

4. The method of claim 1, wherein (c) comprises:
   (i) storing the impedance value.

5. The method of claim 1, wherein the measurement corresponds to a final voltage value of a stimulation pulse.

6. The method of claim 1, wherein (b) further comprises:
   (iv) instructing the implanted device to activate a second lead; and
   (v) repeating (i) and (ii) for each of the at least one electrode that is associated with the second lead.

7. The method of claim 1, further comprising:
   (d) interrogating the implanted device to determine a device type.

8. The method of claim 1, further comprising:
   (d) instructing the implanted device to measure a value of current of the at least one electrode; and
   (e) processing the value of current.

9. The method of claim 8, wherein the at least one electrode comprises at least eight electrodes.

10. The method of claim 1, wherein an amplitude of a stimulation pulse is essentially zero between a repetition of (i) and (ii).

11. A method for automating impedance measurements associated with an implanted device, the method comprising the steps of:
    (a) configuring a parameter of a stimulation pulse of the implanted device;
    (b) performing a measurement process with the stimulation pulse in order to determine an impedance value corresponding to a set of electrodes, wherein step (b) comprises the steps of:
       (i) instructing the implanted device to perform a measurement that is associated with the set of electrodes, wherein the set of electrodes are contained on a lead;
       (ii) calculating the impedance value utilizing the measurement; and
       (iii) restoring an original value of the parameter upon completing step (i) and step (ii), wherein step (i),
       step (ii) and step (iii) are repeated for each set of electrodes that is associated with the lead; and
    (c) automatically processing the impedance value.

12. Apparatus for automating impedance measurements associated with an implanted device, the apparatus comprising:
    a communications module; and
    a processor that communicates with the implanted device through the communications module, the processor configured to perform the steps of:
    (a) configuring a parameter of a stimulation pulse of the implanted device;
    (b) performing a measurement process with the stimulation pulse in order to determine an impedance value corresponding to a set of electrodes; and
    (c) automatically processing the impedance value.

13. The apparatus of claim 12, wherein the set of electrodes comprises a pair of electrodes.

14. The apparatus of claim 12, wherein (c) comprises:
    (i) displaying the impedance value on a user interface.

15. The apparatus of claim 12, wherein (c) comprises:
    (i) storing the impedance value.

16. The apparatus of claim 12, wherein (b) comprises:
    (i) instructing the implanted device to perform a measurement that is associated with the set of electrodes, the set of electrodes contained on a lead; and
    (ii) calculating the impedance value utilizing the measurement.

17. The apparatus of claim 12, wherein the processor is configured to further perform:
    (d) instructing the implanted device to measure a value of current of the set of electrodes; and
    (e) processing the value of current.

18. The apparatus of claim 17, wherein the set of electrodes comprises a pair of electrodes.

19. A method in a computer system for displaying information in order to automate impedance measurements associated with an implanted device, the method comprising:
    (a) displaying an identification of a pair of electrodes;
    (b) displaying a value of impedance that is associated with the pair of electrodes; and
    (c) displaying an indicator that is indicative of a consistency between the value of impedance and a corresponding measured current associated with the pair of electrodes.

20. A method for automating impedance measurements associated with an implanted device, the method comprising:
    (a) configuring a parameter of a stimulation pulse of the implanted device;
    (b) performing a measurement process with the stimulation pulse in order to determine an impedance value corresponding to a set of electrode;
    (c) automatically processing the impedance value;
    (d) displaying an identification of the set of electrodes;
    (e) displaying the value of impedance that is associated with the set of electrodes; and
    (f) displaying a value of current that is measured for the set of electrodes.

* * * * *